United States Patent [19]

Alker et al.

[11] Patent Number: 5,344,835
[45] Date of Patent: Sep. 6, 1994

[54] PIPERIDINE AND PYRROLIDINE DERIVATIVES

[75] Inventors: David Alker, Birchington; Peter E. Cross, Canterbury, both of United Kingdom

[73] Assignee: Pfizer Inc., New York, N.Y.

[21] Appl. No.: 890,595

[22] PCT Filed: Nov. 28, 1990

[86] PCT No.: PCT/EP90/02039
§ 371 Date: Jul. 2, 1992
§ 102(e) Date: Jul. 2, 1992

[87] PCT Pub. No.: WO91/10650
PCT Pub. Date: Jul. 25, 1991

[30] Foreign Application Priority Data

Jan. 6, 1990 [GB] United Kingdom ............ 9000301.3

[51] Int. Cl.$^5$ ............ A61K 31/445; A61K 31/44; C07D 211/12; C07D 409/12
[52] U.S. Cl. ............ 514/317; 514/318; 514/320; 514/321; 514/324; 514/325; 514/326; 514/331; 546/194; 546/196; 546/197; 546/202; 546/204; 546/205; 546/206; 546/213
[58] Field of Search ............ 546/194, 196, 197, 202, 546/204, 205, 206, 213; 514/317, 318, 320, 321, 324, 325, 326, 331

[56] References Cited

U.S. PATENT DOCUMENTS

| | | | |
|---|---|---|---|
| 2,974,146 | 3/1961 | Biel | 260/294.7 |
| 4,810,713 | 3/1989 | Yanni et al. | 514/317 |
| 4,950,674 | 8/1990 | Yanni et al. | 514/317 |

FOREIGN PATENT DOCUMENTS

| | | |
|---|---|---|
| 0350309 | 1/1990 | European Pat. Off. . |
| 934890 | 11/1955 | Fed. Rep. of Germany . |
| 780027 | 7/1957 | United Kingdom . |

*Primary Examiner*—Marianne M. Cintins
*Assistant Examiner*—Phyllis G. Spivack
*Attorney, Agent, or Firm*—Peter C. Richardson; Paul H. Ginsburg; Garth Butterfield

[57] ABSTRACT

According to the invention there is provided a compound of formula (I): $R^1-O(CH_2)_mA(CH_2)_nXR$ or a pharmaceutically acceptable salt thereof, wherein $R^1$ is a group of formula (a or b) where Z is $-(CH_2)_2-$, $-CH=CH-$, $-CH_2-S-$ or $-CH_2-O-$; R is a group of formula (c, d or Het) and A is a group of formula (e, f or g) in which the N atom is attached to the group $(CH_2)n$; m is 1 or 2; n is an integer of from 1 to 4; p is 1, 2 or 3; $R^2$ and $R^3$ are each independently hydrogen, $C_1-C_4$ alkyl, hydroxy-($C_1-C_4$ alkyl), hydroxy, $C_1-C_4$ alkoxy, halo, trifluoromethyl, nitro, cyano, sulphamoyl, $-CO(C_1-C_4$ alkyl), $-OCO(C_1-C_4$ alkyl), carboxy, $-CO_2(C_1-C_4$ alkyl), $-(CH_2)_qCONR^4R^5$, $-(CH_2)_qOCONR^4R^5$, $-(CH_2)_qNR^6R^7$ or $-NHSO_2NH_2$ in which $R^4$ and $R^5$ are each independently H or $C_1-C_4$ alkyl, q is 0, 1 or 2, and either $R^6$ and $R^7$ are each independently H or $C_1-C_4$ alkyl or $R^6$ is hydrogen and $R^7$ is $-SO_2(C_1-C_4$ alkyl), $-CO(C_1-C_4$ alkyl) or $-CONH(C_1-C_4$ alkyl); X is a direct link, O or S; Y and $Y^1$ are each independently O or $CH_2$; and Het is pyridyl, pyrazinyl or thienyl. The compounds are useful as muscarinic receptor antagonists, particularly in the treatment of irritable bowel syndrome.

8 Claims, No Drawings

PIPERIDINE AND PYRROLIDINE DERIVATIVES

BACKGROUND OF THE INVENTION

This invention relates to certain pyrrolidine and piperidine derivatives.

We have discovered that the pyrrolidine and piperidine derivatives provided by the present invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

SUMMARY OF THE INVENTION

German Patentschrift 934890 discloses the preparation of certain benzhydryl ethers. EP-A-0350309 discloses certain 1-arylethyl-3-substituted piperidines as muscarinic receptor antagonists but was published on 10 Jan. 1990.

According to the invention there are provided compounds of the formula:

$$R^1-O(CH_2)_mA(CH_2)_nXR \quad (I)$$

and their pharmaceutically acceptable salts, wherein $R^1$ is a group of the formula:

where Z is $-(CH_2)_2-$, $-CH=CH-$, $-CH_2-S-$ or $-CH_2-O-$; R is a group of the formula:

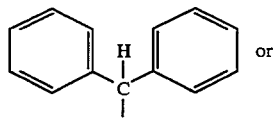

and A is a group of formula:

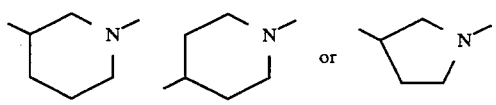

in which
the N atom is attached to the group $(CH_2)n$;
m is 1 or 2;
n is an integer of from 1 to 4;
p is 1, 2 or 3;

$R^2$ and $R^3$ are each independently hydrogen, $C_1-C_4$ alkyl, hydroxy-($C_1-C_4$ alkyl), hydroxy, $C_1-C_4$ alkoxy, halo, trifluoromethyl, nitro, cyano, sulphamoyl, $-CO(C_1-C_4$ alkyl), $-OCO(C_1-C_4$ alkyl), carboxy, $-CO_2(C_1-C_4$ alkyl), $-CH_2)_qCONR^4R^5$, $-(CH_2)_qOCONR^4R^5$, $-CH_2)_qNR^6R^7$ or $-NHSO_2NH_2$ in which $R^4$ and $R^5$ are each independently H or $C_1-C_4$ alkyl, q is 0, 1 or 2, and either $R^6$ and $R^7$ are each independently H or $C_1-C_4$ alkyl or $R^6$ is hydrogen and $R^7$ is $-SO_2(C_1-C_4$ alkyl), $-CO(C_1-C_4$ alkyl) or $-CONH(C_1-C_4$ alkyl);

X is a direct link, O or S;

Y and $Y^1$ are each independently O or $CH_2$; and

Het is pyridyl, pyrazinyl or thienyl.

"Halo means F, Cl, Br or I. Alkyl and alkoxy groups of 3 or 4 carbon atoms can be straight or branched chain. The preferred alkyl and alkoxy groups are methyl, ethyl, methoxy and ethoxy.

Preferably, $R^1$ is $(Ph)_2CH$. m is preferably 1. n is preferably 1, 2 or 3. X is preferably a direct link.

A is preferably a group of the formula:

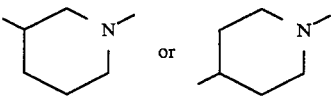

R is preferably a group of the formula:

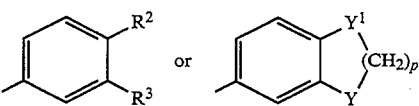

where
$R^2$ and $R^3$ are each independently hydroxymethyl, $C_1-C_4$ alkoxy, $C_1-C_4$ alkoxycarbonyl, carboxy, sulphamoyl, nitro, amino, carbamoyl, sulphamoylamino, $C_1-C_4$ alkanesulphonamido, $-CO(C_1-C_4$ alkyl) or $-NHCO(C_1-C_4$ alkyl);

p is 1 or 2 and Y and $Y^1$ are each O or $CH_2$.

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1–19. These salts can be prepared conventionally, e.g. by mixing a solution of the free base and the acid in a suitable solvent, e.g. ethanol or ether, and recovering the acid addition salt either as a precipitate, or by evaporation of the solution.

DETAILED DESCRIPTION OF THE INVENTION

The compound of the formula (I) can be prepared by the following reaction:

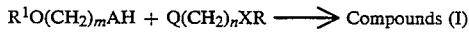

R, $R^1$, A, X, m and n are as defined for formula (I) and Q is a leaving group, e.g. Br, Cl, I, $C_1-C_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium or potassium carbonate, sodium bicarbonate, triethylamine or pyridine, and in a suitable organic solvent, e.g. acetonitrile, at up to the reflux temperature. Reaction temperatures of 60°–120° C. are generally desirable and it is most convenient to carry out the reaction under reflux. Iodo is generally the most suitable leaving group but since the starting materials (III) are generally most conveniently available as chlorides or bromides, the reaction is often most suitably carried out using the compound (III) as a chloride or bromide but in the presence of an iodide such as sodium or potassium iodide. In the preferred technique, the compounds (II) and (III), (III) being in bromide or chloride form, are refluxed together in acetonitrile in the presence of sodium carbonate and sodium iodide. The product (I) can be isolated and purified conventionally.

The starting materials of the formula (III) are in general known compounds which can be prepared by conventional techniques. The preparation of any novel starting materials of the formula (III) used in the Examples is described in the following Preparations section.

The starting materials (II) can be prepared conventionally, e.g. as follows (see also Preparations 1 and 2):

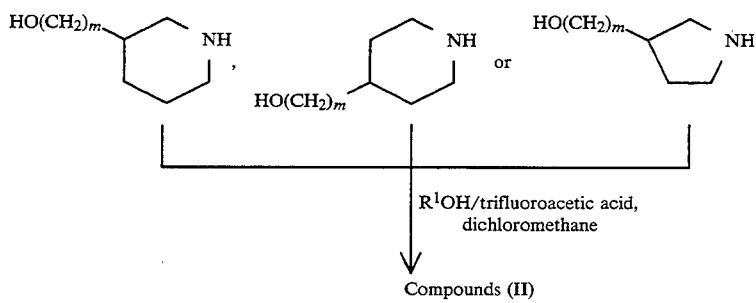

Compounds (II)

The method described in Preparations 7 and 8 can also be used.

Some of the compounds of the formula (I) in which R is a substituted phenyl group can be converted to other compounds of the formula (I) as follows:

(a) A —$CO_2(C_1$–$C_4$ alkyl) substituent on the phenyl group can be reduced to —$CH_2OH$. Lithium aluminium hydride is the most suitable reducing agent. The reaction is typically carried in a suitable organic solvent, e.g. ether, at between 0° and room temperature. It is generally most convenient to use the starting material in the form of its methyl or ethyl ester.

(b) A hydroxy substituent on the phenyl group can be converted to —$OCO(C_1$–$C_4$ alkyl) by acylation using a $C_1$–$C_4$ alkanoyl chloride or bromide or a $C_1$–$C_4$ alkanoic anhydride. The presence of an acid acceptor is preferable. The reaction is typically carried out at about room temperature in a suitable organic solvent, e.g. dioxan.

(c) A —$CO(C_1$–$C_3$ alkyl) substituent on the phenyl group can be reduced to a substituent of the formula —$CH(OH)(C_1$–$C_3$ alkyl). Suitable reducing agents include sodium borohydride and lithium aluminium hydride. The reaction is typically carried out at between 0° and room temperature in a suitable organic solvent, e.g. methanol for sodium borohydride and ether or THF for lithium aluminium hydride. Sodium borohydride is the preferred reducing agent.

(d) A —$CO_2(C_1$–$C_4$ alkyl) substituent, preferably —$CO_2CH_3$, can be converted to —$CONR^4R^5$ by reaction with ammonia or the appropriate amine $R^4R^5NH$. When $R^4$ and $R^5$ are both H, the use of aqueous (0.0880) ammonia is generally most convenient, although the reaction can be carried out using ammonia in an organic solvent such as methanol or ethanol, or ammonia neat in a bomb. Although in some instances the reaction with the amines $R^4R^5NH$ may proceed at a satisfactory rate at room temperature, heating at up to 120°, preferably 60° to 100° C., is generally necessary. For volatile amines, the reaction is best carried out in a bomb.

(e) A nitro substituent on the phenyl group can be reduced to amino by conventional means. The preferred reducing agent is stannous chloride dihydrate and the reaction is typically carried out in an organic solvent such as ethanol under reflux.

(f) An amino substituent on the phenyl group can be converted to —$NHSO_2(C_1$–$C_4$ alkyl) by reaction with a $C_1$–$C_4$ alkanesulphonyl chloride or bromide or $C_1$–$C_4$ alkanesulphonic anhydride, typically in an organic solvent such as dioxane. The presence of an acid acceptor such as pyridine, triethylamine, sodium bicarbonate or sodium or potassium carbonate, is preferable. It is sometimes convenient, particularly when a sulphonyl chloride is used, to carry out the reaction in pyridine, the pyridine functioning as both the solvent and the acid acceptor. Heating is not usually necessary: normally the reaction will proceed at a satisfactory rate at room temperature.

(g) A substituent of the formula —$(CH_2)_qNH_2$ where q is 0, 1 or 2 can be converted to —$(CH_2)_qNHCO(C_1$–$C_4$ alkyl) by reaction with a $C_1$–$C_4$ alkanoyl chloride or bromide or $C_1$–$C_4$ alkanoic anhydride. The reaction can be carried out similarly to (f) above. The use of acetic anhydride in acetonitrile with triethylamine as the acid acceptor is a preferred reaction.

(h) An amino substituent on the phenyl group can also be converted to sulphamoyl by reaction with sulphamide, typically under reflux in an organic solvent such as dioxane.

(i) A hydroxy substituent can be converted to $C_1$–$C_4$ alkoxy firstly by reaction with a strong base such as sodium hydride, and then by reaction with a $C_1$–$C_4$ alkyl iodide. The reaction is preferably carried out at about room temperature in a solvent such as dimethylformamide.

(j) A hydroxy substituent of the formula —$(CH_2)_qOH$ where q is 0, 1 and 2 can be converted to —$(CH_2)_qOCONH(C_1$–$C_4$ alkyl) by reaction with a $C_1$–$C_4$ alkyl isocyanate. The reaction is typically carried out at about room temperature in a solvent such as methylene chloride.

(k) A hydroxymethyl substituent on the phenyl group can be converted to —$CH_2NR^6R^7$ where $R^6$ and $R^7$ are independently H or $C_1$-$C_4$ alkyl by reaction firstly with thionyl chloride and secondly with ammonia or the appropriate amine $R^6R^7NH$. The reaction with thionyl chloride is typically carried out with heating, preferably under reflux, in a solvent such as methylene chloride. The reaction with ammonia or the amine is typically carried out at about room temperature in a solvent such as ethanol.

(l) An acetyl substituent can be converted to —C(OH)(CH$_3$)$_2$ by reaction with methyllithium, methylmagnesium bromide, methylmagnesium iodide or methylmagnesium chloride. The reaction is typically carried out in a solvent such as ether at a temperature of from 0° C. to room temperature.

(m) an iodo substituent can be converted to $C_1$-$C_4$ alkoxycarbonyl by reaction, typically at about room temperature, with carbon monoxide in a $C_1$-$C_4$ alkanol containing a base [e.g. potassium carbonate] and a palladium (II) catalyst [e.g. bis(triphenylphosphine)palladium (II) chloride].

(n) A cyano substituent on the phenyl group can be reduced to aminomethyl, typically by catalytic hydrogenation, e.g. using $H_2$/Pd/C in ethanol containing a small amount of concentrated hydrochloric acid.

(o) A substituent of the formula —$(CH_2)_qNH_2$ were q is 0, 1 or 2 can be converted to a substituent of the formula —$(CH_2)_qNHCONH(C_1$-$C_4$ alkyl) by reaction with a $C_1$-$C_4$ alkyl isocyanate. The reaction is typically carried out at about room temperature in a solvent such as methylene chloride.

(p) A $C_1$-$C_4$ alkoxy substituent, preferably methoxy, can be converted to hydroxy by treatment with a $C_1$-$C_4$ alkanethiol in the presence of a strong base, e.g. sodium hydride. The reaction is typically carried out by refluxing the reactants in a suitable solvent, e.g. dimethylformamide. Butanethiol is the preferred thiol.

(q) A carboxy substituent can be converted to carbamoyl by reaction with oxalyl chloride and then ammonia in e.g. dichloromethane at about room temperature, and (r) a $C_1$-$C_4$ alkoxycarbonyl substituent can be hydrolysed to carboxy using e.g. aqueous alkali, preferably aqueous sodium hydroxide, in e.g. dioxane.

The selectivity of the compounds as muscaranic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1-5 minute contact time for each does of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiolgoical salt solution containing the second concentration of test compound and the above procedure is repeated. Typically four concentrations of the test compound are evaluated on each tissue.

The concentration of the test compound which causes a doubling of the agonist concentration required to produce the original response is determined ($pA_2$ value—Arunlakshana and Schild (1959), Brit. J. Pharmacol. 14, 48-58). Using the above analytical techniques, tissue selectivity for muscarinic receptor antagonists is determined.

Activity against agonist induced bronchoconstriction, gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose to cause a doubling of pupil size is determined as well as the dose to inhibit by 50% the salivation and tremor responses to intravenous oxotremorine.

For administration to man in the curative or prophylactic treatment of diseases associated with the altered motility and/or tone of smooth muscle, such as irritable bowel syndrome, diverticular disease, urinary incontinence, oesphageal achalasia and chronic obstructive airways disease, oral dosages of the compounds will generally be in the range of from 3.5 to 350 mg daily for an average adult patient (70 kg). thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case bu there can, of course, be individual instances where higher or lower dosage rates are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The following Examples, in which all temperatures are in 0° C., illustrate the invention:

EXAMPLE 1
3-(Diphenylmethoxymethyl)-1-(3-methoxyphenethyl)-piperidine

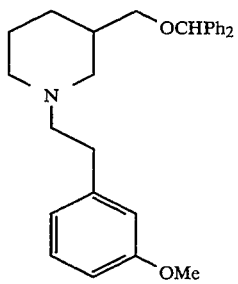

A mixture of 3-(diphenylmethoxymethyl)piperidine (1.40 g, 5.0 mmol—see Preparation 1), 3-methoxyphenethyl bromide (1.08 g, 5.0 mmol), sodium carbonate (1.08 g) and sodium iodide (0.10 g) in acetonitrile (30 ml) was heated under reflux for 18 hours, diluted with ethyl acetate and water and the layers separated. The organic layer was washed with water, dried over magnesium sulphate and evaporated. The residue was purified by chromatography on silica using dichloromethane plus 0–3% methanol as eluant. Appropriate fractions were combined and evaporated to give the title compound (1.12 g) as a colourless oil which was characterised containing a third of an equivalent of water.

Analysis: Found: C,79.8; H,7.8; N,3.5; $C_{28}H_{33}N_2.0.33H_2O$ requires: C,79.8; H,7.8; N,3.3.

EXAMPLE 2–6

The following compounds were prepared by reacting 3-(diphenylmethoxymethyl)piperidine with the appropriate alkylating agent of the formula $R(CH_2)_n Hal$ in the presence of $NaI/Na_2CO_3$ as described in Example 1. The free base products from Examples 4 and 5 were each converted to their hydrochloride salts by treatment of a solution in ether with excess ethereal hydrogen chloride followed by evaporation. The residue obtained in Example 5 was crystallised from ethyl acetate.

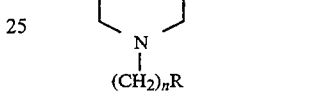

| Example No | n | Hal | R | Form characterised | Analysis % (Theoretical in brackets) | | |
|---|---|---|---|---|---|---|---|
| | | | | | C | H | N |
| 2 | 2 | Br | benzodioxole (O-CH2-O) | free base, 0.75 hydrate, oil | 76.4 (76.2) | 7.3 (7.6) | 2.9 (3.1) |
| 3 | 2 | Br | C(O)Me-phenyl | free base, oil | 81.2 (81.5) | 7.9 (7.7) | 3.2 (3.3) |
| 4 | 1 | Cl | benzodioxole | hydrochloride hemihydrate, foam | 70.5 (70.3) | 6.7 (6.8) | 2.8 (3.0) |
| 5 | 3 | Br | OMe-phenyl | hydrochloride, m.p. 156–158° C. | 74.3 (74.7) | 7.8 (7.8) | 3.1 (3.0) |
| 6 | 2 | Br | benzodioxole | free base, hydrate, oil. | 77.0 (76.7) | 7.4 (7.3) | 2.9 (3.2) |

EXAMPLE 7

4-(Diphenylmethoxymethyl)-1-(3-methoxyphenethyl)-piperidine

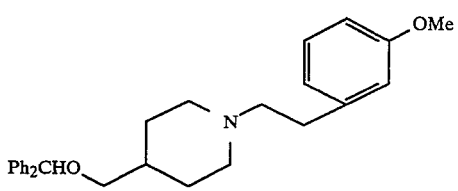

A mixture of 4-(diphenylmethoxymethyl)piperidine (1.40 g, 5.0 mmol—see Preparation 2), 3-methoxyphenethyl bromide (1.08 g, 5.0 mmol), sodium carbonate (1.06 g) and sodium iodide (0.50 g) in acetonitrile (30 ml) was heated under reflux for 16 hours, diluted with ethyl acetate and water and the layers separated. The organic layer was washed with water, dried over magnesium sulphate and evaporated. The residue was purified by chromatography on silica using dichloromethane plus 0–5% methanol as eluant. Appropriate fractions were combined and evaporated to give the title compound (1.12 g) as a colourless oil.

Analysis: Found: C,80.4; H,8.0; N,3.4; $C_{28}H_{33}NO_2$ requires: C,81.0; H,7.95; N,3.4.

EXAMPLE 8-17

The following compounds were prepared by reacting 4-(diphenylmethoxymethyl)piperidine with the appropriate alkylating agent of the formula $R(CH_2)_n Hal$ in the presence of $NaI/Na_2CO_3$ as described in Example 7 and were characterised in the form indicated. In those cases where the form characterised was the hydrochloride salt, these were prepared by treating a solution of the appropriate free base in ether with excess ethereal hydrogen chloride. The resulting precipitated oil or solid was collected, washed with ether and dried to give the desired compound.

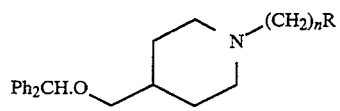

| Example No | n | Hal | R | Form characterised | Analysis % (Theoretical in brackets) | | |
|---|---|---|---|---|---|---|---|
| | | | | | C | H | N |
| 8 | 1 | Cl | ![benzodioxole] | hydrochloride, hemihydrate foam | 7.0 (70.3) | 6.7 (6.8) | 3.0 (3.0) |
| 9 | 3 | Cl | ![OMe phenyl] | hydrochloride, 0.25 hydrate foam | 74.2 (74.0) | 7.8 (7.8) | 2.9 (3.0) |
| 10 | 2 | Br | ![OMe phenyl] | hydrochloride hemihydrate m.p. 158–160° C. | 72.7 (72.9) | 7.7 (7.6) | 3.1 (3.0) |
| 11 | 1 | Cl | ![CO2Et phenyl] | hydrochloride, m.p. 172–174° C. | 72.6 (72.6) | 7.1 (7.2) | 2.9 (2.8) |
| 12 | 2 | Cl | ![SO2NH2 phenyl] | hydrochloride, hemihydrate, foam | 63.5 (63.6) | 6.5 (6.7) | 5.6 (5.5) |
| 13 | 2 | Br | ![NO2 phenyl] | hydrochloride foam | 69.1 (69.4) | 7.0 (6.7) | 5.8 (6.0) |
| 14 | 2 | Cl | ![CO2Me phenyl] | hydrochloride hemihydrate m.p. 166–168° C. | 71.3 (71.2) | 7.0 (7.2) | 2.9 (2.9) |
| 15 | 2 | Br | ![benzodioxole] | hydrochloride, foam | Characterised by its $^1$H-NMR spectrum | | |

| Example No | n | Hal | R | Form characterised | Analysis % (Theoretical in brackets) |||
|---|---|---|---|---|---|---|---|
| | | | | | C | H | N |
| 16 | 2 | Br |  OH | free base, m.p. 115–117° C. | Characterised by its $^1$H-NMR spectrum |||
| 17 | 1 | Cl | 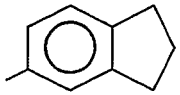 | free base foam | 84.2 (84.6) | 8.2 (8.1) | 3.5 (3.4) |

EXAMPLE 16

$^1$H-NMR (CDCl$_3$) δ=7.2–7.45 (14H,m) 5.38 (1H,s), 4.68(2H,s), 3.39(2H, d, J=4 Hz), 3.20(2H, d J=6 Hz), 2.91–3.01, (2H,m), 2.68–2.82 (2H,m), 2.23 (3.20(2H, t, J=6 Hz), 1.75–2.0(3H,m) and 1.50–1.70(2H,m).

EXAMPLE 15

$^1$H-NMR (CDCl$_3$) δ=7.2–7.45 (10H,m), 6.60–6.82 (3H,m), 5.96 (2H,s), 5.37 (1H,s), 3.37(2H, d, J=4 Hz), 2.5–3.15 (6H,m) 1.6–2.15 (5H,m), and 1.25–1.50 (2H,m).

EXAMPLE 18

4-(Diphenylmethoxymethyl)-1-(4-hydroxymethylbenzyl)piperidine hydrochloride

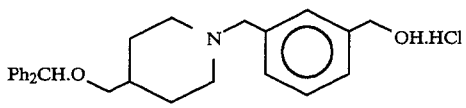

A solution of 4-(diphenylmethoxymethyl)-1-(4-ethoxycarbonylbenzyl)piperidine (0.79 g, 1.8 mmol) (see Example 11), in ether (5 ml) was added dropwise over 5 minutes to a stirred suspension of lithium aluminium hydride (68 mg, 1.8 mmol) in ether (5 ml) and the mixture stirred at room temperature for 1 hour, quenched by the cautious sequential addition of water (0.07 ml), 15% aqueous sodium hydroxide solution (0.07 ml) and water (0.21 ml) and filtered. The filtrate was dried over magnesium sulphate and treated with excess ethereal hydrogen chloride. The mixture was decanted and the residual oil triturated with ether to give the title compound (0.70 g) as a colourless foam.

Analysis %: Found: C,73.6; H,7.5; N,3.2; C$_{27}$H$_{31}$NO$_2$.HCl requires: C,74.0; H,7.45; N,3.2.

EXAMPLE 19

1-(4-Carboxyphenethyl)-4-(diphenylmethoxymethyl)piperidine hydrochloride

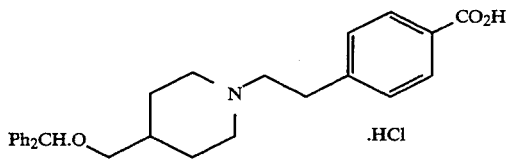

A mixture of 4-(diphenylmethoxymethyl)-1-(4-methoxycarbonylpenethyl)piperidine (1.40 g, 3.2 mmol) (see Example 14) and sodium hydroxide (0.38 mg, 9.5 mmol) in a mixture of dioxane (20 ml) and water (20 ml) was stirred at 100° C. for 2 hours, allowed to cool to room temperature, acidified with acetic acid and evaporated. The residue was partitioned between ethyl acetate and water and the layers separated. The aqueous layer was extracted into ethyl acetate and the combined organic layers were dried over magnesium sulphate and evaporated. The residue was dissolved in ethyl acetate and the solution treated with excess ethereal hydrogen chloride. The resulting precipitate was collected, washed with ethyl acetate and dried to give the title compound (1.03 g) as an off-white solid, m.p. 209–212° C. decomp.

Analysis %: Found: C,72.0; H,7.0; N,3.0; C$_{23}$H$_{31}$NO$_3$.HCl requires: C,72.2; H,6.95; N,3.0.

EXAMPLE 20

1-(4-Carboxamidophenethyl)-4-(diphenylmethoxymethyl)piperidine

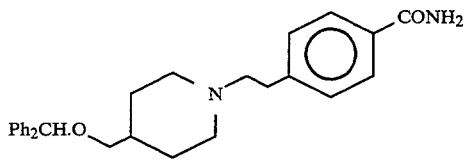

Oxalyl chloride (272 mg, 2.14 mmol) was added dropwise to a stirred suspension of 1-(4-carboxyphenethyl)-4-(diphenylmethoxymethyl)piperidine hydrochloride (0.50 g, 1.07 mmol) (see Example 19) and N,N-dimethylformamide (2 drops) in dichloromethane (20 ml) and the mixture stirred at room temperature for 1 hour. Gaseous ammonia was then bubbled through the solution for 15 minutes and the mixture evaporated. The residue was partitioned between ethyl acetate and 10% aqueous potassium carbonate solution and the layers separated. The aqueous layer was extracted into ethyl acetate and the combined organic layers were dried over magnesium sulphate and evaporated. The residue was crystallised from ethyl acetate to give the title compound (250 mg) as an off-white solid, m.p. 172°–174° C., which was characterized as a hemihydrate.

Analysis %: Found: C,77.2; H,7.5; N,6.7; C$_{28}$H$_{32}$N$_2$O$_2$.0.5H$_2$O requires: C,76.8; H,7.6; N,6.4.

EXAMPLE 21

1-(4-Aminophenethyl)-4-(diphenylmethoxymethyl)-piperidine

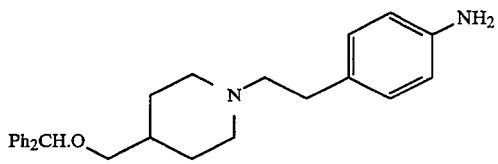

A mixture of 4-(diphenylmethoxymethyl)-1-(4-nitrophenethyl)piperidine (1.40 g, 3.3 mmol) (see Example 13) and stannous (II) dichloride dihydrate (3.68 g, 16.3 mmol) in ethanol (20 ml) was heated at 70° C. for 2 hours, allowed to cool to room temperature and filtered. The filtrate was evaporated and the residue partitioned between ethyl acetate and saturated aqueous sodium hydrogen carbonate solution. The layers were separated and the aqueous layer extracted into ethyl acetate. The combined organic layers were washed with saturated brine, dried over magnesium sulphate and evaporated. The residue was triturated with ether and the resulting solid collected, washed with ether and dried to give the title compound (0.66 g) as a fawn solid, m.p. 188°–190° C., which was characterized by its $^1$H-NMR spectrum.

$^1$H-NMR (CDCl$_3$) δ=7.20–7.45 (10H,m) 7.04 (2H,d,J=8 Hz), 6.63(2H, d,J=8 Hz), 5.37 (1H,s), 3.55–3.8 (4H,m), 3.40 (2H,broad s), 3.05–3.25 (4H,m), 2.55–2.75 (2H,m) and 1.80–2.20 (5H,m).

EXAMPLE 22

4-(Diphenylmethoxymethyl)-1-(4-sulphamoylaminophenethyl)piperidine

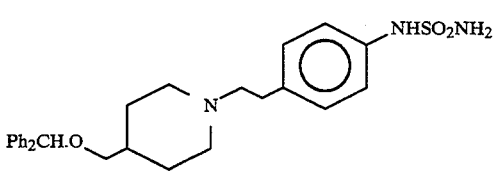

A solution of 1-(4-aminophenethyl)-4-(diphenylmethoxymethyl)piperidine (200 mg, 0.50 mmol) (see Example 21) and sulphamide (480 mg, 5.0 mmol) in dioxane (5 ml) was heated under reflux for 3 hours and evaporated. The residue was partitioned between ethyl acetate and 10% aqueous potassium carbonate solution and the layers separated. The aqueous layer was extracted into ethyl acetate and the combined organic layers were dried over magnesium sulphate and evaporated. The residue was purified by chromatography on silica using dichloromethane plus 0–4% methanol as eluant. Appropriate fractions were combined and evaporated and the residue triturated with diisopropyl ether. The resulting solid was collected, washed with diisopropyl ether and dried to give the title compound (100 mg) as a pale yellow solid, m.p. 172°–174° C., which was characterised by its $^1$H-NMR spectrum.

$^1$H-NMR (CDCl$_3$) δ=7.0–7.5 (14H,m), 5.37 (1H,s), 4.6–5.6 (3H, broad s), 3.34 (2H,d,J=4 Hz), 3.02–3.20 (2H,m), 2.55–2.90 (4H,m), 2.0–2.25 (2H,m), 1.5–1.90 (5H,m).

EXAMPLE 23

4-(Diphenylmethoxymethyl)-1-(4-methanesulphonamidophenethyl)piperidine hydrochloride

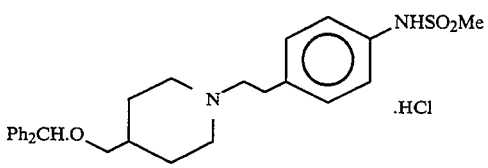

Methanesulphonyl chloride (69 mg, 0.60 mmol) was added dropwise to a stirred solution of 1-(4-aminophenethyl)-4-(diphenylmethoxymethyl)piperidine (200 mg, 0.50 mmol) (see Example 21) and triethylamine (61 mg, 0.60 mmol) in dioxane (5 ml) and the mixture heated under reflux for 2 hours and evaporated. The residue was partitioned between ethyl acetate and 10% aqueous potassium carbonate solution. The layers were separated and the aqueous layer extracted into ethyl acetate. The combined organic layers were dried over magnesium sulphate and evaporated. The residue was purified by chromatography on silica using dichloromethane plus 0–4% methanol as eluant. Appropriate fractions were combined and evaporated. The residue was dissolved in ether and the solution treated with excess ethereal hydrogen chloride. The mixture was decanted and the residual oil was washed with ether and dried to give the title compound (90 mg) as a pale yellow foam which was characterised containing 0.25 equivalents of water.

Analysis %: Found: C,64.7; H,7.1; N,5.2; C$_{28}$H$_{34}$N$_2$O$_3$S.HCl.0.25H$_2$O requires: C,64.7; H,6.9; N,5.4.

EXAMPLE 24

1-(4-Acetamidophenethyl)-4-(diphenylmethoxymethyl)piperidine

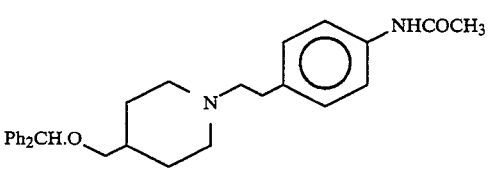

Acetic anhydride (68 mg, 0.67 mmol) was added dropwise to a stirred solution of 1-(4-aminophenethyl)-4-(diphenylmethoxymethyl)piperidine (180 mg, 0.45 mmol) (see Example 21) and triethylamine (55 mg, 0.54 mmol) in acetonitrile (5 ml) and the mixture heated under reflux for 2 hours and evaporated. The residue was partitioned between ethyl acetate and 10% aqueous potassium carbonate and the layers separated. The aqueous layer was extracted into ethyl acetate and the combined organic layers were dried over magnesium sulphate and evaporated. The residue was triturated with ethyl acetate and the resulting solid collected, washed with ethyl acetate and dried to give the title compound (35 mg) as an off-white solid which was characterised containing 0.25 equivalents of water.

Analysis %: Found: C,77.8; H,7.7; N,6.4; C$_{29}$H$_{34}$N$_2$O$_2$.0.25H$_2$O requires: C,77.9; H,7.8; N,6.3.

EXAMPLE 25

3-(Diphenylmethoxymethyl)-1-(3-methylenedioxyphenethyl)pyrrolidine

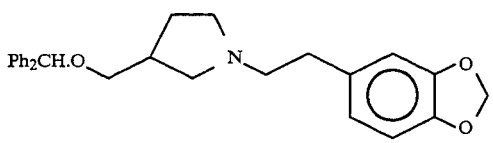

A mixture of 3-(diphenylmethoxymethyl)pyrrolidine (267 mg) (Preparation 7), 3,4-methylenedioxyphenethyl bromide (250 mg), sodium carbonate (1.0 g) and sodium iodide (100 mg) in acetonitrile (30 ml) was heated under reflux for 24 hours, diluted with water and ethyl acetate and the layers separated. The organic layer was washed with water, dried over magnesium sulphate and evaporated. The residue was purified by chromatogrpahy on silica using dichloromethane plus 0–20% ethyl acetate followed by dichloromethane plus 20% ethyl acetate plus 1–5% methanol as eluant. Appropriate fractions were combined and evaporated to give the title compound (217 mg) as a colourless oil which was characterised containing 0.25 equivalents of water.

Analysis %: Found: C,77.0; H,7.1; N,3.3; $C_{27}H_{29}NO_3 \cdot 0.25 \, H_2O$ requires: C,77.2; H,7.0; N,3.3.

EXAMPLE 26

3-(Diphenylmethoxymethyl)-1-(3,4-methylenedioxybenzyl)pyrrolidine

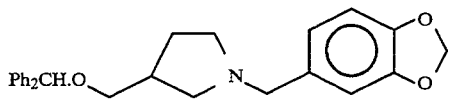

This was prepared as described in Example 25 using 3,4-methylenedioxybenzyl chloride instead of 3,4-methylenedioxyphenethyl bromide. The title compound was obtained as a colourless oil.

Analysis %: Found: C,77.7; H,6.9; N,3.5; $C_{26}H_{27}NO_3$ requires: C,77.8; H,6.7; N,3.5.

PREPARATION 1

3-(Diphenylmethoxymethyl)piperidine

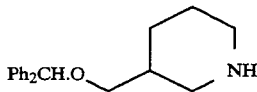

Trifluoroacetic acid (20 ml) was added cautiously to a vigorously stirred solution of piperidine-3-methanol (5.75 g, 50 mmol) in dichloromethane (20 ml) and the mixture treated with benzhydrol (9.2 g, 50 mmol) portionwise over 5 minutes, stirred at room temperature for 2 hours and evaporated. The residue was dissolved in dioxane (50 ml) and the solution treated with 4M aqueous sodium hydroxide solution (100 ml), stirred at room temperature for 2 hours, diluted with ether and water and the layers separated. The organic layer was washed with water and extracted into 2M hydrochloric acid. The acidic extract was washed with ether, basified with solid sodium carbonate, extracted into ether, washed with water, dried over magnesium sulphate and evaporated to give the title compound (4.31 g) as a pale yellow oil which was characterised by its $^1$H-NMR spectrum.

$^1$H-NMR (CDCl$_3$) δ=7.2–7.45 (10H,m) 5.34 (1H,s), 3.18–3.36 (3H,m) 3.03 (1H,dt,J=8 and 2 Hz), 2.57 (1H,tt,J=10 and 2.5 Hz), 2.39 (1H,dd,J=10 and 8 Hz) and 1.1–1.95 (6H,m).

PREPARATION 2

4-(Diphenylmethoxymethyl)piperidine

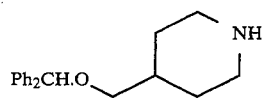

This was prepared as described in Preparation 1 using piperidine-4-methanol instead of piperidine-3-methanol. The title compound was obtained as a colourless oil.

Analysis %: Found: C,81.5; H,8.4; N,5.3; $C_{19}H_{23}NO$ requires: C,81.1; H,8.2; N,5.0.

PREPARATION 3

3,4-Methylenedioxyphenethyl alcohol

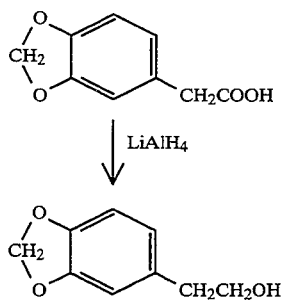

3,4-Methylenedioxyphenylacetic acid (18.0 g) was added portionwise over 30 minutes to a stirred, ice-cooled suspension of lithium aluminium hydride (4.0 g) in ether (400 ml) and the mixture was stirred at room temperature for two hours, quenched by the cautious addition of saturated aqueous ammonium chloride solution and filtered. The filtrate was washed with 10% aqueous sodium carbonate solution, dried over magnesium sulphate and evaporated to give the title compound as a pale yellow oil (15.0 g), which was characterised by its $^1$H-NMR spectrum.

$^1$H-NMR (CDCl$_3$) δ=6.69–6.83 (3H,m) 5.98 (2H,s), 3.82 (2H, dt, J=7 and 6 Hz), 2.81 (2H,t,J=7 Hz), and 1.44 (1H,t,J=6 Hz, exchangeable with D$_2$O).

PREPARATION 4

3,4-Methylenedioxyphenethyl bromide

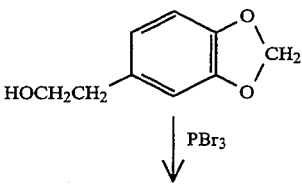

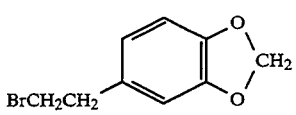

A solution of phosphorus tribromide (8.1 g) in carbon tetrachloride (50 ml) was added dropwise over 30 minutes to a stirred solution of 3,4-methylenedioxyphenethyl alcohol (15.0 g) (see Preparation 3) in carbon tetrachloride (200 ml) and the mixture was heated under reflux for 3 hours, washed sequentially with water (twice), 5M aqueous sodium hydroxide solution and water, dried over magnesium sulphate and evaporated. The residue was purified by chromatography on silica (100 g) using carbon tetrachloride as the eluant. Appropriate fractions were combined and evaporated to give the title compound as a pale yellow oil (8.3 g), which was characterised by its $^1$H-NMR spectrum.

$^1$H-NMR (CDCl$_3$) δ=6.80 (1H,d,J=8 Hz), 6.75 (1H,s); 6.71 (1H,d, J=8Hz); 6.00 (2H,s); 3.56 (2H,t,J=7 Hz) and 3.13 (2H,t,J=7Hz).

PREPARATION 5

6-(2-Hydroxyethyl)benzodioxan

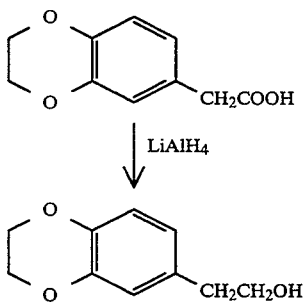

This was prepared as described in Preparation 3 using (benzodioxan-6-yl)acetic acid instead of 3,4-methylenedioxyphenylacetic acid. The title compound was obtained as a colourless oil which was characterised by its $^1$H-NMR spectrum.

$^1$H-NMR (CDCl$_3$) δ=6.84 (1H,d,J=8 Hz); 6.77 (1H,d,J=2 Hz); 6.73 (1H,dd, J=8 and 2 Hz); 4.28 (4H,s); 3.59 (2H,t,J=8 Hz) and 3.08 (2H,t,J=7 Hz).

PREPARATION 6

6-(2-Bromoethyl)benzodioxan

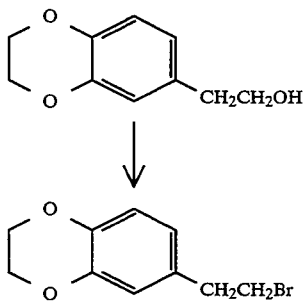

This was prepared as described in Preparation 4 using 6-(2-hydroxyethyl)benzodioxan (see Preparation 5) instead of 3,4-methylenedioxyphenethyl alcohol. The title compound was obtained as a pale yellow oil which was characterised by its $^1$H-NMR spectrum.

$^1$H-NMR (CDCl$_3$) δ=6.83 (1H,d,J=8 Hz); 6.77 (1H,d,J=2 Hz); 6.72 (1H,dd, J=8 and 2 Hz); 4.28 (4H,s); 3.59 (2H,t,J=7 Hz) and 3.10 (2H,t,J=7Hz).

PREPARATION 7

3-(Diphenylmethoxymethyl)pyrrolidine

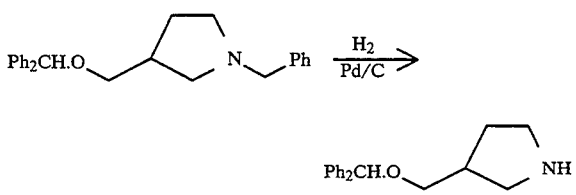

A solution of 1-benzyl-3-(diphenylmethoxymethyl)-pyrrolidine (1.43 g, Preparation 8) in ethanol (50 ml) containing acetic acid (1.0 ml) was stirred at room temperature for six days under an atmosphere of hydrogen in the presence of 5% palladium on charcoal. The mixture was filtered and the filtrate was diluted with ethyl acetate, washed with 10% aqueous sodium carbonate solution and water, dried over magnesium sulphate and evaporated to give the title compound (0.84 g) as a pale yellow oil which was characterised by its $^1$H-NMR spectrum.

$^1$H-NMR (CDCl$_3$) δ=7.25–7.45 (10H,m) 5.35 (1H,s), 2.4–3.5 (8H, m), 1.83–2.05 (1H,m) and 1.42–1.58 (1H,m).

PREPARATION 8

1-Benzyl-3-(diphenylmethoxymethyl)pyrrolidine

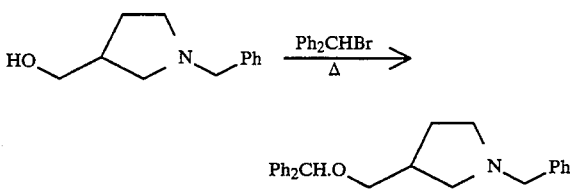

A mixture of 1-benzylpyrrolidine-3-methanol (1.72 g) (J. Org. Chem., 1961, 26, 1521) and bromodiphenylmethane (4.94 g) in xylene (150 ml) was heated under reflux for 3 hours, allowed to cool to room temperature, diluted with ethyl acetate, washed with 10% aqueous sodium carbonate solution, dried over magnesium sulphate and evaporated. The residue was purified by chromatography on silica using dichloromethane plus 20% ethyl acetate plus 0–10% methanol as eluant. Appropriate fractions were combined and evaporated to give the title compound (1.57 g) as a pale brown oil which was charcterised by its $^1$H-NMR spectrum.

$^1$H—NMR (CDCl$_3$)δ=7.15–7.6 (15H,m), 5.35 (1H, s), 4.01 (2H, AB, J=14 Hz), 3.47(2H, d,J=7 Hz), 2.65–3.45 (5H, m), 2.12–2.32 (1H, m) and 1.75–1.91(1H, m).

We claim:

1. A compound of the formula:

$$R^1-O(CH_2)_mA(CH_2)_nXR \qquad (I)$$

or a pharmaceutically acceptable salt thereof, wherein $R^1$ is a group of the formula:

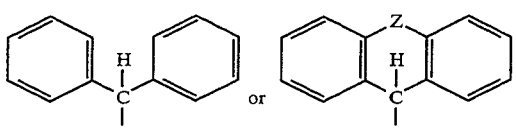

where Z is —(CH$_2$)$_2$—, —CH=CH—, —CH$_2$—S— or —CH$_2$—O—; R is a group of the formula:

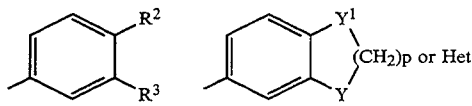

and A is a group of formula:

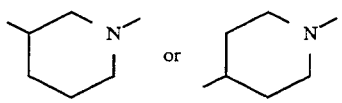

in which
the N atom is attached to the group (CH$_2$)n;
m is 1 or 2;
n is an integer of from 1 to 4;
p is 1, 2 or 3;
R$^2$ and R$^3$ are each independently hydrogen, C$_1$–C$_4$ alkyl, hydroxy-(C$_1$–C$_4$ alkyl), hydroxy, C$_1$–C$_4$ alkoxy, halo, trifluoromethyl, nitro, cyano, sulphamoyl, —CO(C$_1$–C$_4$ alkyl), —OCO(C$_1$–C$_4$ alkyl), carboxy, —CO$_2$(C$_1$–C$_4$ alkyl), —CH$_2$)$_q$CONR$^4$R$^5$, —(CH$_2$)$_q$NR$^6$R$^7$ or —NHSO$_2$NH$_2$ in which R$^4$ and R$^5$ are each independently H or C$_1$–C$_4$ alkyl, q is 0, 1 or 2, and either R$^6$ and R$^7$ are each independently H or C$_1$–C$_4$ alkyl or R$^6$ is hydrogen and R$^7$ is —SO$_2$(C$_1$–C$_4$ alkyl), —CO(C$_1$–C$_4$ alkyl) or —CONH(C$_1$–C$_4$ alkyl);
X is a direct link, O or S;
Y and Y$^1$ are each independently O or CH$_2$; and
Het is pyridyl or thienyl.

2. A compound as claimed in claim 1 in which R$^1$ is (Ph)$_2$CH.

3. A compound as claimed in claim 1 in which m is 1.

4. A compound as claimed in claim 3 in which n is 1, 2 or 3.

5. A compound as claimed in claim 4 wherein X is a direct link.

6. A compound as claimed in claim 5 in which R is a group of the formula

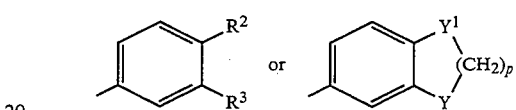

where
R$^2$ and R$^3$ are each independently hydroxymethyl, C$_1$–C$_4$ alkoxy, C$_1$–C$_4$ alkoxycarbonyl, carboxy, sulphamoyl, nitro, amino, carbamoyl, sulphamoylamino, C$_1$–C$_4$ alkanesulphonamido, —CO(C$_1$–C$_4$ alkyl) or —NHCO(C$_1$–C$_4$ alkyl);
p is 1 or 2 and Y and Y$^1$ are each O or CH$_2$.

7. A pharmaceutical composition comprising a compound of formula (I) as claimed in claim 1, or a pharmaceutically acceptable salt thereof, and a pharmaceutically acceptable diluent or carrier.

8. A method of treating irritable bowel syndrome in a patient in need of such treatment, comprising administering to said patient an effective amount of a compound of the formula (I) or a pharmaceutcally acceptable salt thereof as claimed in claim 1.

* * * * *